US006322783B1

(12) United States Patent
Takahashi

(10) Patent No.: US 6,322,783 B1
(45) Date of Patent: Nov. 27, 2001

(54) BACTERIOPHAGES, METHOD FOR SCREENING SAME AND BACTERICIDAL COMPOSITIONS USING SAME, AND DETECTION KITS USING SAME

(76) Inventor: Seishi Takahashi, 245-18, Tsunashima, Mobara-shi, Chiba 297 (JP)

( * ) Notice: Subject to any disclaimer, the term of this patent is extended or adjusted under 35 U.S.C. 154(b) by 0 days.

(21) Appl. No.: 09/242,901

(22) PCT Filed: Aug. 26, 1997

(86) PCT No.: PCT/JP97/02957

§ 371 Date: Feb. 26, 1999

§ 102(e) Date: Feb. 26, 1999

(87) PCT Pub. No.: WO98/08944

PCT Pub. Date: Mar. 5, 1998

(30) Foreign Application Priority Data

Aug. 26, 1996 (JP) .................................................. 8-261132
Apr. 19, 1997 (JP) .................................................. 9-135716

(51) Int. Cl.[7] .................................................. A01N 63/00
(52) U.S. Cl. ...................... 424/93.6; 424/543; 435/235.1
(58) Field of Search ............................... 424/404, 78.01, 424/543, 93.6; 435/235.1

(56) References Cited

U.S. PATENT DOCUMENTS 4,851,240 * 7/1989 Day et al. ............................. 426/53
5,660,812 * 8/1997 Merril et al. .......................... 424/9.2

OTHER PUBLICATIONS

Soothill, Journal of Medical Microbiology vol. 37 p 258–261, 1992.*
Smith et al. Journal of General Microbiology vol. 128 p 307–318, 1982.*
Smith et al. Journal of General Microbiology vol. 129 p 2659–2675, 1983.*
Ronner and Cliver 1990 Journal of Food Protection vol. 53, No. 11 pp. 944–947.*

* cited by examiner

*Primary Examiner*—Donna C. Wortman
*Assistant Examiner*—Robert A. Zeman
(74) *Attorney, Agent, or Firm*—Shanks & Herbert

(57) ABSTRACT

The bacteriophage has a high level of specificity to a certain specific pathogenic bacterium so that the bacteriophage can surely kill the pathogenic bacterium as a host through phogocytic action. The bio-bactericidal material containing the bacteriophage can be applied to food such as fresh food, etc., and to places, etc. or to even persons for cooking food material such as restaurants, school kitchens, etc., or any other thing which requires disinfection from pathogenic bacteria, and it can kill pathogenic bacteria. The bio-bactericidal material containing a cocktail of two or more different kinds of the bacteriophages can kill corresponding kinds of pathogenic bacteria concurrently. Further, the phage can infect only the pathogenic bacterium as a host bacterium, and does not infect persons, making it very safe and useful.

2 Claims, 2 Drawing Sheets

BACTERIOPHAGES, METHOD FOR SCREENING SAME AND BACTERICIDAL COMPOSITIONS USING SAME, AND DETECTION KITS USING SAME

TECHNICAL FIELD

The present invention relates to a novel bacteriophage, a method for screening the same as well as a novel bactericidal composition using the same and a detection kit using the same. More particularly, the present invention relates to a novel bacteriophage having a high specificity against a variety of pathogenic bacteria, including the pathogenic *Escherichia coli,* a method for screening such pathogenic bacteria as well as a novel bactericidal composition using such a bacteriophage singly or in combination of two or more different kinds of bacteriophages as a cocktail, a stabilizer for storing the same in a stable manner, and a reagent and a detection kit for detecting the pathogenic bacteria by the bacteriophage.

BACKGROUND TECHNOLOGY

A variety of bacteria are distributed widely in nature, and many out of such bacteria are playing a significant role in natural phenomena including, e.g., decomposition, fermentation, etc. On the other hand, such bacteria also include so-called pathogenic bacteria with which animals including, for example, human beings, pets such as dogs, cats, etc. and plants are infected and which cause diseases and blights. Many bacteria may also invade the tissues of animals and plants and propagate therein, thereby causing diseases and blights.

*Escherichia coli* is one of such pathogenic bacteria, and exists everywhere in the nature. *E. coli* is always present in the intestines of human beings and other mammals. Under regular circumstances, *E. coli* is not hazardous to human beings and other mammals. However, among the various strains of *E. coli,* pathogenic bacteria such as intestinal hemolytic *E. coli* may cause serious infection under some conditions in human beings and other mammals.

In order to prevent infection from such pathogenic bacteria such as, e.g., pathogenic *E. coli* or to treat the infection from such bacteria, a number of bactericides have been used. The bactericides may include iodo tincture solution, merculon chlorhexizine and the like. These have been extensively employed for the disinfection of wounds. Further, preservatives such as, e.g., benzoic acid are employed for food. Moreover, a variety of effective antibiotics have been employed for the prevention and treatment of infection from bacteria.

When there is a risk of infection from a pathogenic *E. coli,* such as intestinal hemolytic *E. coli,* it occurs through materials such as raw ox liver or vegetables such as radish shoots, lettuce, etc. In cases where infection from pathogenic bacterium, i.e. intestinal hemolytic *E. coli,* has recently been occurred, it is also suspected that the infection has been caused via sashimi (raw fish slices) or rare steak, etc. It will be noted that iodo tincture solution or merculon could not be employed as bactericides for controlling infection through food such as fresh food, etc., due to their toxicity. Further, it is also impossible to use antibiotics in the prevention or treatment of bacterial infections of food.

Even if a bactericide existed which were safe for use in food, it would be very difficult to spray the food with it uniformly. If the bactericide were sprayed irregularly on the food, there would be a difference in the concentration of the bactericide, and the bactericidal effects would be localized, leaving areas where bacteria would still be alive, thereby resulting in serious problems with infection.

Substances such as, e.g. polylysine, etc., are known to control the multiplication of bacteria. They have bacteriostatic action, although they do not have the bactericidal action. When polylysine is applied for the purpose of controlling the multiplication of bacteria, it has to be used in concentrations as high as 0.5% to 1%. If it would be used with food in such high concentrations, it is readily anticipated that taste of the food may be changed. Further, it is expensive and irregularities in the level of concentrations may be anticipated.

Currently, there is no known bactericidal substance that is non-toxic to human beings when applied to food such as fresh food. Therefore, the current situation is that food such as fresh vegetables, particularly those to be used for school meals, etc., are disinfected with hot water. There needs to be a bactericidal material that can be applied to food, such as fresh food, etc. and that is safe to human beings.

It should be noted that a bacteriophage (hereinafter referred to sometimes as a "phage") consists only of protein and nucleic acids, and may be classified as an organism which can propagate only in a specific bacterium as a specific host bacterium. It is an abiotic material that it is so minute that it can be observed only through an electron microscope. It is known that such a bacteriophage can infect only a specific bacterium as a host bacterium and it can propagate by eating up the infected bacterium. Presently, there are a large number of bacteriophages which are known to infect a variety of bacteria as hosts. Such bacteriophages may include, for example, phages peculiar to Salmonella as a host and phages peculiar to vibrio as a host. Further, there are known phages which utilize *E. coli* as a host and have destructive phagocytic action against *E. coli.* About three hundred kinds of such phages are known and a great number are present in the air. Each of the bacteriophages causes the infection of *E. coli* but it is non-toxic to human beings and other mammals. Likewise, there are known phages which use bacteria other than *E. coli* as hosts. These do not cause infection, and are non-toxic to human beings and other mammals.

It is also known that bacteriophages infect bacteria only, or a very small number of specific bacteria, and it has a high specificity of bacteria hosts. For instance, phages which infect one type of *E. coli* only may not infect any other different kinds of *E. coli.* For instance, it is known that a well known species, i.e. T2 phage, cannot infect C-type *E. coli.* Such bacteriophages have so far been used only as objects of research, and they have greatly served to develop genetic research. However, they have yet to attract an attention for their application to industry, due to their high specificity. Therefore, such bacteriophages have never been used as a bactericide.

Although many bacteriophages are known to utilize a variety of bacteria as hosts in the manner as described above, it is not yet known if there is any bacteriophage which utilizes a pathogenic bacterium such as, e.g. intestinal hemolytic *E. coli,* as a host.

Of the bacteria which act as hosts for bacteriophages, particularly *E. coli* is extremely high in multiplication, and its cells divide once every 20 to 30 minutes. If conditions permit, one cell of *E. coli* propagates up to 1 gram for one day. However, *E. coli* is present everywhere in nature and exists in the intestine of human beings and the other mammals, and yet it does not usually harm human beings or other mammals. Therefore, many so-called biomedicines are produced from *E. coli* cultures because of its properties.

Although there has not yet been discovered a bacteriophage which can utilize pathogenic bacterium such as intestinal hemolytic *E. coli* as a host, nor potential bacteriophages been found by conventional screening methods. A method for screening such bacteriophages with high efficiency and certainty needs to be established yet. Specifically, a screening method that can select such bacteriophages efficiently and surely must be developed.

Further, no bactericide effective for direct application to food, such as fresh food, etc. is currently available commercially. It has also been demanded to develop a product that can be applied directly to food, such as fresh ones, etc.

In order to develop such a bactericide, it is also necessary to develop a stabilizer or a preservative that can ensure safety when the such bactericide is applied directly to food, such as fresh food, etc. and allow for storage over a long period of time.

To date, buffers such as, e.g. tris-HCl, phosphate, etc., have been used as an effective phage storing solution; however, they have only been used so far for research purposes, and cannot be applied directly to food, such as fresh food, etc. Moreover, there is no known phage storing solution that can be sprayed directly onto fresh food and that can be taken into the human body through the mouth.

In the event that food poisoning is caused by an infection from a pathogenic bacterium, it takes several days at the present time to determine which pathogenic bacterium has caused the food poisoning. It is therefore necessary to identify the causal infective bacterium in the shortest possible period of time. This would enable the treatment of food poisoning as soon as possible, for the effective identification of pathogenic bacterium such as intestinal hemolytic *E. coli.* For these reasons, a need has been established for the development of a detection reagent and a reagent kit for detecting pathogenic bacterium such as, e.g. intestinal hemolytic *E. coli,* etc.

DISCLOSURE OF INVENTION

In order to meet the demands as described above, the present inventor has conducted extensively research on the specific actions of bacteriophages and found that a certain kind of a specific bacteriophage can kill a specific pathogenic bacterium, even when the bactericidal material contains a bacteriophage which has been applied directly to food, such as fresh food, etc. It can kill such a pathogenic bacterium as well as ensure the safety of food, such as fresh food.

The present invention therefore has the primary object to provide a bacteriophage that can demonstrate an extremely high level of specificity to only pathogenic bacterium.

Further, the present invention has another object to provide a screening method that can efficiently and certainly select a bacteriophage which has a high level of specificity to particular pathogenic bacterium.

The present invention has a further object to provide a bio-bactericidal material which contains a bacteriophage that can ensure an extremely high degree of safety even when the bacteriophage is applied directly to food, such as fresh food, and which can stabilize the phage for a long period of time.

Moreover, the present invention has a still further object to provide a phage stabilizer for stabilizing the bacteriophage in bio-bactericidal material for long periods of time, while at the same time ensuring an extremely high level of safety even upon direct application to food, such as fresh food.

In addition, the present invention has a still further object to provide a phage detection kit or a reagent kit for detecting a pathogenic bacterium as a host bacterium with a high level of efficiency and certainty in a short period of time, by taking advantage of the phagocytosis of the bacteriophage.

It is to be understood herein that the term "pathogenic bacterium" referred to in this description is intended to mean a bacterium which animals, such as human beings and dogs, cats, etc., are infected, causing a disease or a symptom of a disease and which is destroyed as a host of the bacteriophage by the phagocytic action of the bacteriophage. The term "pathogenic bacterium" is a generic term for such pathogenic bacteria such as, e.g., intestinal hemolytic *E. coli,* etc. Further, it is to be understood herein that the description of *E. coli* is as a representative of pathogenic bacteria, and that *E. coli* is described as being illustrative of pathogenic bacteria. The present invention is construed as being not limited to this specific example.

In order to achieve the objects as described above, the present invention in one aspect provides a bacteriophage which has a high level of specificity to only pathogenic bacterium.

The present invention further provides a novel bacteriophage with a high level of specificity to a specific kind of pathogenic *E. coli* and can meet extensive demands by using the bacteriophage effectively for a variety of pathogenic bacteria, including pathogenic *E. coli.*

As a preferred mode of the one aspect, the present invention also provides a screening method for efficiently and surely screening a bacteriophage which has a high level of specificity to only pathogenic bacterium.

Further, the present invention provides novel bio-bactericidal material containing a bacteriophage that has a high level of specificity to only pathogenic bacteria. Such novel bio-bactericidal material can be applied directly to food, such as fresh food, by taking advantage of the action of the bacteriophage contained therein, and does not adversely affect humans or other mammals whatsoever. It also can destroy infectious pathogenic bacteria via phagocytosis.

Furthermore, the novel bio-bactericidal material according to the present invention may comprise a cocktail containing two or more different kinds of bacteriophages so that it can simultaneously compete with the plurality of different pathogenic bacteria.

Moreover, as the novel bio-bactericidal material according to the present invention contains a stabilizer or storage material for a storing liquid to stably preserve the bacteriophage for a long period of time, it can be stored for a long period of time while ensuring and sustaining a high level of safety and stability.

In another aspect, the present invention provides a method for producing a culture liquid of a bacteriophage characterized in that host bacteria growing in a culture medium are infected with the bacteriophages and the bacteriophages propagate therein to yield the culture liquid thereof In a preferred mode of this aspect of the present invention, the method for the production of the bacteriophage can propagate specific bacteriophages having a particularly high level of specificity to pathogenic bacteria by adding calcium ions to the culture medium in which the pathogenic bacteria are being cultured.

Further, the present invention provides a stabilizer or storage material for the storing liquid of the bacteriophage, which allows the culture liquid of the bacteriophages to be stored in a stable manner for a long period of time.

In a further aspect, the present invention provides a detection kit for detecting a pathogenic bacterium, which can detect the presence or absence of the pathogenic bacterium with certainty in a speedy and simplified manner by taking advantage of the specific bacteriophage.

BRIEF DESCRIPTION OF THE DRAWINGS

In FIG. 3, reference symbol (a) indicates a petri dish in which only an agar medium was cultured and reference symbol (b) indicates a petri dish in which intestinal hemolytic *E. coli* O-157 was cultured. In this drawing, it can be found that the petri dish turned white due to the multiplication of the intestinal hemolytic *E. coli* O-157. FIG. 3(*c*) indicates an example of a culture in which a mother liquid of the phage ($2\times10^{10}$/ml) capable of eating only the intestinal hemolytic *E. coli* O-157 was added to an agar culture medium together with the intestinal hemolytic *E. coli* O-157. This figure indicates that all the intestinal hemolytic *E. coli* O-157 were eaten up and destroyed. FIG. 3(*d*) shows an example of an agar culture in which intestinal hemolytic *E. coli* O-157 was diluted to 1,000 times with the phage storing liquid according to the present invention to yield a dilution ($2\times10^{7}$/ml) thereof and the dilution was added to the agar culture together with the intestinal hemolytic *E. coli* O-157. This figure indicates that all the intestinal hemolytic *E. coli* O-157 has been eaten up and thoroughly destroyed. FIG. 3(*e*) illustrates an example of an agar culture in which the 1,000-fold dilution ($2\times10^{7}$/ml) of the intestinal hemolytic *E. coli* O-157 with the phage storing liquid according to the present invention was further diluted to a 20-fold dilution with tap water and the resulting dilution was then added to the agar culture together with the intestinal hemolytic *E. coli* O-157. This figure indicates that all the intestinal hemolytic *E. coli* O-157 has been eaten up and destroyed thoroughly. FIG. 3(*f*) illustrates an example of an agar culture in which the 1,000-fold dilution ($2\times10^{7}$/ml) of the intestinal hemolytic *E. coli* O-157 with the phage storing liquid according to the present invention was further diluted to a 100-fold dilution with tap water and the resulting dilution was added to the agar culture together with the intestinal hemolytic *E. coli* O-157. This illustration indicates that all the intestinal hemolytic *E. coli* O-157 has been eaten up and thoroughly destroyed.

Figure 1:
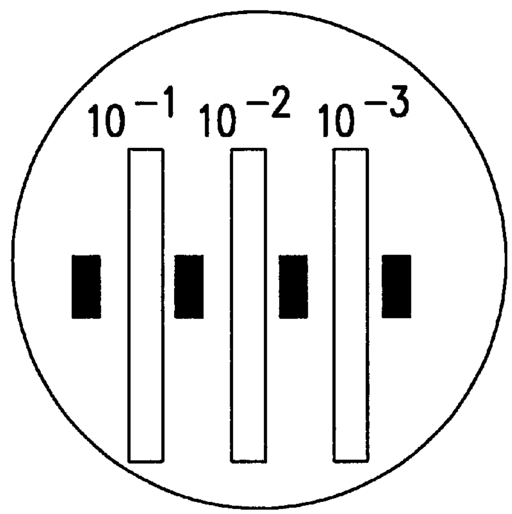
FIG. 1 is an illustration showing the bactericidal effects on a plate by the cross-streak method. In the illustration, it is shown that the bacteria in contact with a test bacteriophage are killed completely.
Figure 2:
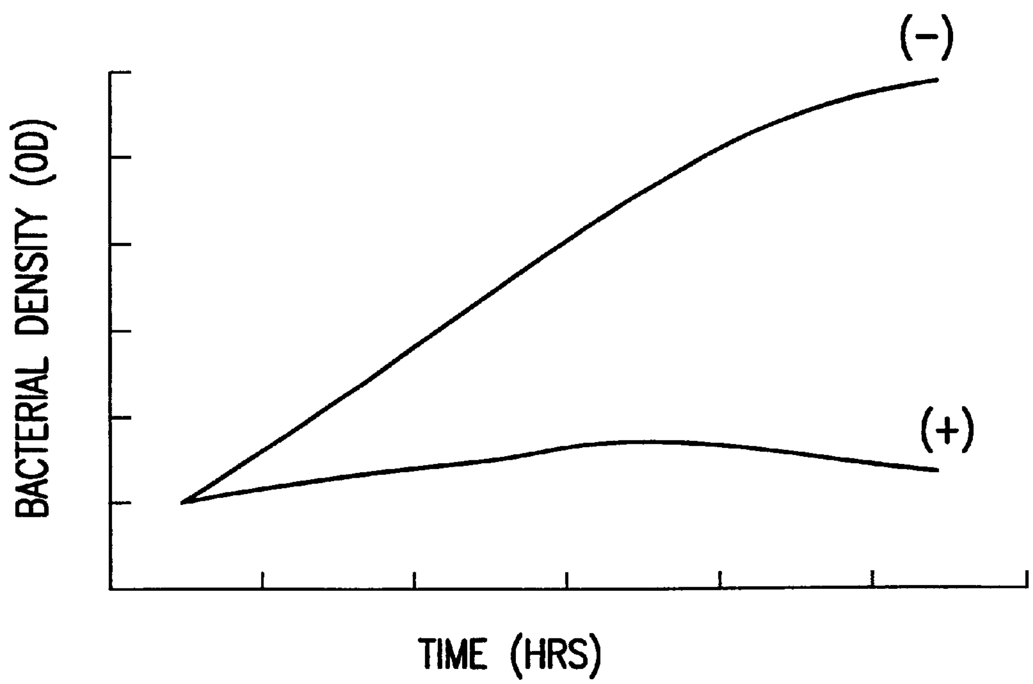
FIG. 2 is an illustration showing the effects of the material according to the present invention in a liquid culture. In this illustration, the reference symbol (−) indicates a multiplication curve of a bacterium when no material according to the present invention is added and the reference symbol (+) indicates complete control over the multiplication of the bacterium when the material according to the present invention is added when the MOI (Multiplicity of Infection) rate equals 10.
Figure 3A:
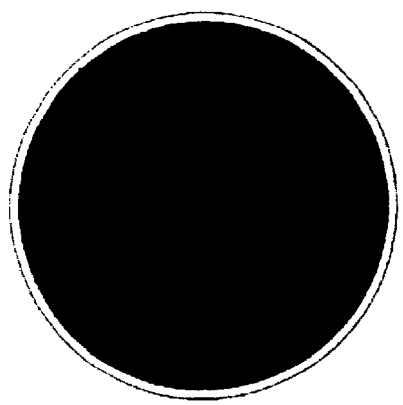
FIG. 3 is an illustration showing the culture state of the bacteriophage according to the present invention.
Figure 3B:
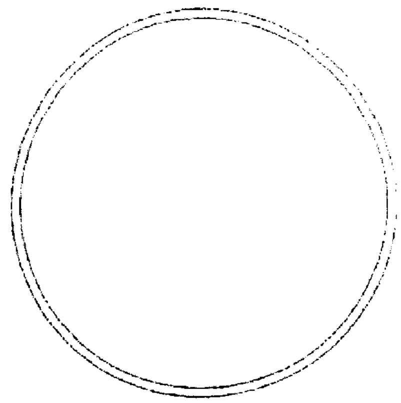
Figure 3C:
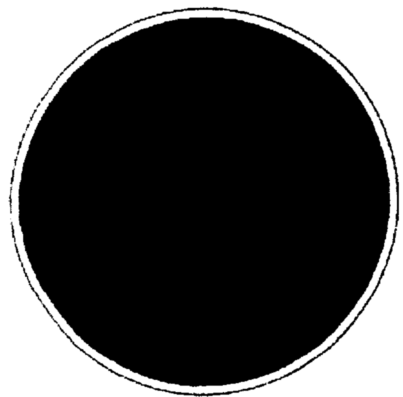
Figure 3D:
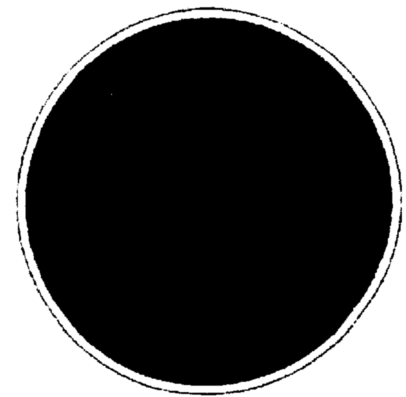
Figure 3E:
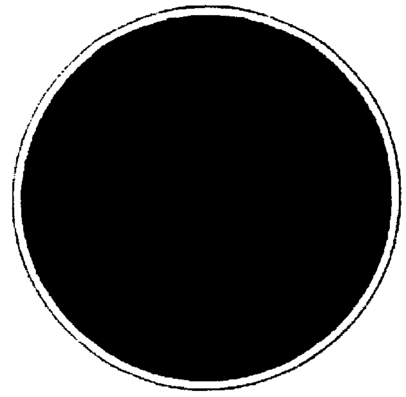
Figure 3F:
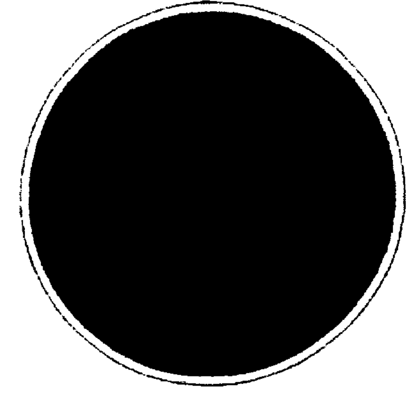

BEST MODES FOR CARRYING OUT THE INVENTION (Bacteriophage)

It is well known that a bacteriophage is present in the excretions of various animals, including livestock such as, e.g. cattle, etc., pets such as, e.g. dogs, cats, etc., birds such as, e.g. pigeons, crows, etc., poultry such as, e.g. chickens, etc., or in sewage and the like and that it can be isolated from the excretions and sewage.

In accordance with the present invention, any kind of bacteriophages can be employed in order to achieve the objects of the present invention, regardless of its source, as long as it has a high specificity to pathogenic bacteria including, for example, pathogenic *E. coli* such as, e.g. intestinal hemolytic *E. coli,* etc., and the bacteriophage to be employed for the present invention is not limited to any particular type. In other words, there may be employed any bacteriophage that can achieve the objects of the present invention by absorbing its specific host bacterium and destroy it. Such bacteriophages may include, for example, *E. coli*-specific bacteriophage such as the T-series phages (T1, T2, T3, T4, T5, T7, etc.), phage ΦX-174, phage λ, phage ΦX80, phage Qβ, phage P1, or any other *E. coli*-specific phages which may be obtained by the screening method according to the present invention. In addition to *E. coli,* there may be mentioned, for example, bacteriophages such as, e.g. phage SZP01 and SP02, etc., which are specific to *Bacillus subtilis.*

Among such bacteriophages, in particular, there are some which are characterized by DNA including fragments that have base sequences as indicated by SEQ ID NOS 1–4, SEQ ID NOS 5–14, SEQ ID NOS 15–19, and SEQ ID NOS 20–24. Each of these, as will be described below, has a high level of specificity to intestinal hemolytic *E. coli* O-157. The DNA sequences of those bacteriophages are identified by the method which is described below.

(Screening of Bacteriophage)

It is found that a large number of bacteriophages which have hitherto been employed in the research of molecular biology cannot lyse pathogenic bacteria as in the present invention, including, for example, pathogenic *E. coli* such as, e.g. intestinal hemolytic *E. coli,* etc.

A conventional screening method for screening a bacteriophage may be employed in order to select bacteriophages which have a high level of specificity in accordance with the present invention. No screening method has been established yet, however, which can select a bacteriophage that has a high level of specificity to a pathogenic bacterium, particularly pathogenic *E. coli* such as, e.g. intestinal hemolytic *E. coli,* etc. In order to enhance the efficiency and certainty of screening, a method for screening the bacteriophage has been modified in a manner that will be described below, and it is found that the screening method can identify a bacteriophage from Nature. This can lyze a pathogenic *E. coli,* particularly including, e.g. intestinal hemolytic *E. coli,* with a high level of specificity.

In accordance with the present invention, samples are collected from the excrement of various animals and from sewage. The samples collected are then screened for a bacteriophage having a high level of specificity to a pathogenic bacterium which might exist therein. The screening method may comprise, for instance, infecting a host with a bacteriophage sought to be contained in the sample. The host comprising, for example, *E. coli* strains K, B and C, having a restriction enzyme of minus ($r^-$) and a modification enzyme of positive ($m^+$), amplify the bacteriophage contained in the sample by plating the lysate with the pathogenic bacterium and isolating a single plaque. These steps are repeated several times to amplify the phages, thereby forming a high titer stock. Thereafter, only a substantially thoroughly lytic and clear plaque is selected and the selected plaque is allowed to have contact with EDTA for several hours at high temperature (55° C.–65° C.). Only naturally occurring phage containing a deleted DNA is selected. By repeating this operation at several times, a phage having stable and essential genes can be selected.

(Culture of Bacteriophage)

A description will now be made of the method for culturing a novel bacteriophage according to the present invention by using as an example a culture of a bacteriophage of *E. coli* as a host.

First, *E. coli* is cultured at room temperature or at an elevated temperature in a culturing device such as, e.g. a jar fermentor, etc. The culture medium contains, e.g. polypeptone, yeast extract, etc., until the number of cells of *E. coli* is propagated to a desired number. At the stage when the number of cells of *E. coli* is propagated to, for example, 2 to $3\times10^8$ per ml of the culture medium (e.g., OD=0.2), the bacteriophage is then added to the culture medium. After the bacteriophage has been added to the culture medium, the culture is maintained under substantially the same conditions as the previous culture in order to allow the *E. coli* to be infected with the bacteriophage and the bacteriophage to be propagated in the cells of the *E. coli* leading the bacteriophage to completely destroying the *E. coli.* As a consequence, when the culture is maintained for a predetermined period of time, a culture liquid of the bacteriophage in which no surviving *E. coli* is obtained. The culture liquid is then purified in accordance with a conventional method to remove *E. coli* of residues and so on in a conventional way, for example, by centrifugation or the like, thereby yielding a purified culture liquid of the bacteriophage.

The bacteriophage according to the present invention may also be cultured in an agar culture medium containing, for example, polypeptone, yeast extract and so on. In this culture, it may be possible to use a two-layer agar culture medium with the layers having different agar concentrations. The culture using such a two-layer agar culture medium may be carried out by adding *E. coli* and phages to the upper layer and incubating the culture medium at room temperature or at elevated temperature. The resulting culture of the phages may then be processed by adding the phage storing liquid or the like to the agar culture medium in order to dissolve the agar culture medium therein and separating solid materials, e.g. residues of the culture medium, etc., from a supernatant by centrifugation of the resulting mixture or by other conventional means, thereby yielding the resulting supernatant as a mother liquid of the phage.

It is to be noted that the surface of *E. coli* has a receptor configuration capable of absorbing a bacteriophage. The bacteriophage is allowed to be absorb by the *E. coli* through this receptor configuration. This allows the injection of, e.g., DNA and RNA, i.e., genes of the bacteriophage itself, into the cell of *E. coli.* Once the DNA and RNA are absorbed into the cell of *E. coli,* the bacteriophage begins to propagate, and eat the cell of *E. coli* in a short time. As the bacteriophage continues to propagate in the cell of *E. coli,* the *E. coli* is eventually destroyed, leading an increase in the bacteriophages in the culture liquid and forming a culture liquid of the bacteriophages. It is to be noted that the mechanism can be said to be substantially identical to the case where pathogenic bacteria are killed by the bio-bactericidal material according to the present invention containing the bacteriophage.

In the culturing of the bacteriophage as described above, when the bacteriophage utilizes a pathogenic *E. coli* such as intestinal hemolytic *E. coli* as a host, it is preferred to add a minute amount of a metal such as magnesium, manganese, calcium or the like to the culture medium for culturing *E. coli.* In some cases, it is required to use particularly calcium ions in the culture medium. A chemical substance may also be employed so long as it can release calcium ions into the culture medium for *E. coli,* and that it does not adversely affect the culturing of *E. coli* and the bacteriophage. Such a chemical substance may include, for example, calcium chloride or the like.

(Stabilization of a Phage Storing Liquid)

In order to store the culture of the bacteriophage according to the present invention for a long period of time, it is preferred to add a buffer solution containing a salt and a minute amount of a metal such as, e.g. Mg, Mn, Ca, etc. to the culture liquid. In order to further stabilize the culture liquid, it may be possible to add glycerol at a rate of approximately 0.001% to 5%, preferably from approximately 0.1% to 1%. Moreover, there may be added a saccharide including, for example, a polysaccharide such as, e.g., maltose, glucose, etc., an amino acid such as, e.g., glycine, arginine, lysine, etc., ethylparabene, polylysine, and the like.

In order to stabilize the bacteriophage contained in the novel phage storing liquid according to the present invention while ensuring a high level of safety to food, the novel bacteriophage storing liquid may contain an amino acid such as, e.g., glycine, arginine, lysine, etc., preferably glycine. When an amino acid is added to the phage storing liquid, it may contain a buffer solution in the amount of from approximately 10 mM to 1 M, preferably from 50 mM to 500 mM, while at the same time adjusting the pH value of the solution to pH 6–8, and preferably to pH 6.5–7.5. Sodium chloride may be added optionally at the rate of up to approximately 5%, and preferably from approximately 0.03% to 1%. Calcium chloride may be added in the amount of up to 10 mM, and preferably from the range of approximately 0.1 mM to 1 mM.

Further, the novel bacteriophage storing liquid according to the present invention is found that the bacteriophage contained therein is not caused to be inactivated upon dilution with normal tap water to approximately 100 times and it can demonstrate a sufficiently strong level of phagocytosis for killing the pathogenic bacteria and destroying them. On the other hand, when the phage storing liquid is diluted with alkaline water or acidic water for domestic use, it is likewise found that the bacteriophage contained therein is not inactivated and it can demonstrate a strong level of phagocytosis.

(Novel Bio-bactericidal Material)

The novel bio-bactericidal material using the bacteriophage according to the present invention may be prepared in a manner as will be described hereinafter.

Specifically, the culture liquid of the bacteriophage obtained by incubation in the manner as described above may then be subjected to separation by conventional procedures, such as centrifugation, etc., to separate the liquid portion from a solid culture medium residue. The resulting liquid portion of the culture liquid may then be used as a mother liquid for the bio-bactericidal material according to the present invention. It is preferable that the culture liquid according to the present invention contains bacteriophage cells in the number of approximately $10^2$ to $10^{12}$ per ml, and preferably from approximately $10^3$ to $10^8$ per ml.

The bio-bactericidal material according to the present invention may contain a single kind of a bacteriophage, or two or more different kinds of bacteriophages, as a cocktail; the combination of the plural different kinds of the bacteriophages as a cocktail may be varied appropriately according to the needs and purposes of the bio-bactericidal material according to the present invention. In the use of the several kinds of the bacteriophages to be used as a cocktail, as a matter of course, the respective hosts of pathogenic bacteria can be killed and broken simultaneously.

The mother liquid of the bio-bactericidal material according to the present invention as prepared in the manner as described above contains the bacteriophage in a concentration which is usually higher than required. For this reason, it is preferable to dilute it to an appropriate concentration. The dilution of the mother liquid of the bio-bactericidal material may be carried out preferably with the phage storing liquid prepared in the manner as described above, although it may be diluted with tap water or the like.

Moreover, when the bio-bactericidal material according to the present invention is used as a cocktail in which two or more different kinds of the bacteriophages are combined together, it can offer advantages in controlling the occurrence of resistant bacteria to be otherwise caused due to frequent use. More specifically, when there is used the bio-bactericidal material according to the present invention containing phage T2 and phage λ in equal amounts in order to prevent the occurrence of resistant bacteria against the respective phages due to frequent use in killing the pathogenic bacteria, it is found that the frequency of occurrence of the respective resistant bacteria may be as low as $10^{-12}$. It is found from this result that the frequency of occurrence can be controlled to a negligibly low level both experimentally as well as theoretically. On the other hand, when the bio-bactericidal material according to the present invention containing phage T2 and phage λ each is used, it is found that the frequency of occurrence of the corresponding resistant bacterium may be as high as $10^{-6}$.

Furthermore, the bio-bactericidal material according to the present invention may contain a bactericide for use with food, such as benzoic acid, etc., at the rate ranging from approximately 0.002% to 2%, and preferably from approximately 0.1% to 0.3%, in order to enhance stability of the bio-bactericidal material of the present invention.

In addition, the bio-bactericidal material according to the present invention is odorless and tasteless so that a flavoring material such as lemon flavor, etc., may be added thereto when it is employed together with a food material.

When the mechanism of the action of the bio-bactericidal material according to the present invention is described by taking pathogenic *E. coli* as an example, the bacteriophage may be substantially equal to the rate of propagation of *E. coli,* and destroying *E. coli* completely upon culturing the bacteriophage.

More specifically, *E. coli* has a receptor structure which absorbes the bacteriophage on its surface. The bacteriophage can be absorbed by *E. coli* through its receptor structure, and is able to inject its own genes, i.e. DNA and RNA, etc. into the cell of *E. coli.* Once the substances, such as DNA and RNA, are injected into the cell of *E. coli,* the bacteriophage eats the *E. coli* up, and propagates in the cell of *E. coli* within a short period of time. As the bacteriophages propagate in the cell of *E. coli,* it destroys *E. coli* completely and consequently kill it. Therefore, the bio-bactericidal material according to the present invention has a mechanism of action which is thoroughly different from other bactericides conventionally employed. Accordingly, the bio-bactericidal material according to the present invention can be said to be a bactericidal material or a bactericidal agent having the bactericidal action resulting from the phagocytic action, rather than a conventional bactericide. The bactericidal material according to the present invention is called a novel bio-bactericidal material containing bacteriophages.

Because the bio-bactericidal material according to the present invention has the bactericidal action, due to the mechanism of action as described above, the bacteriophages can eat up all the cells of *E. coli* and kill *E. coli* so that irregularities in the concentration of the bio-bactericidal material cause no difference in the bactericidal action of the phage. Even if only one cell of the bacteriophage were absorbed on the cell of the pathogenic *E. coli,* the pathogenic *E. coli* cell would be eaten up and killed as time elapses. Therefore, the bio-bactericidal material according to the present invention presents the advantage that it can be employed even in an extremely low concentration.

(Reagent and a Reagent Kit for Detecting Bacteriophage)

The bacteriophage according to the present invention can be employed as a reagent for detecting a pathogenic bacterium acting as a host for the corresponding bacteriophage. As the bacteriophage can eat up the cell of *E. coli* as the host and kill it, it can be prepared as a reagent for detecting the pathogenic bacterium acting as the host therefor by taking advantage of the phagocytic action of the bacteriophage. Further, a reagent kit using the phage may be prepared in a variety of types. For example, an agar culture medium may be injected into a container such as a petri dish and prepared so as to culture the bacteriophage. The reagent kit of this type may be applied in stages, for instance, which may comprise coating the surface of the agar culture medium containing the bacteriophage with a sample of the test material that might contain the pathogenic bacterium to be detected and incubating the culture medium at an appropriate temperature. If the pathogenic bacterium to be detected exists in the sample, the bacteriophage contained in the culture medium would eat up the pathogenic bacterium and lyze it, thereby making the culture medium transparent or translucent at the lytic location. When such a transparent or translucent spot is detected in the culture medium, it can be determined that the test sample contains the pathogenic bacterium that corresponds to the bacteriophage contained in the agar culture medium as a detection reagent and that the corresponding pathogenic bacterium is detected.

For instance, when pathogenic *E. coli* is to be detected as the pathogenic bacterium, the pathogenic *E. coli* can be divided and propagated within a very short period of time so that it may be determined in 30 minutes whether a sample contains *E. coli* to be detected after the agar culture medium detection reagent kit is coated with the sample. In other words, it is extremely convenient that the pathogenic bacteria such as, e.g., *E. coli,* etc. can be detected within a period of time as short as 30 minutes by the use of the phage according to the present invention. Further, it is very useful to use the detection reagent or the reagent kit according to the present invention because *E. coli* can surely be detected due to the phagocytic action of the phage constituting the detection reagent or the reagent kit even if the pathogenic bacterium to be detected is present in a very small amount of the sample.

Moreover, when the detection reagent or the reagent kit according to the present invention contains two or more different kinds of phages, the corresponding different kinds of the pathogenic bacteria can be detected simultaneously. This is also a very useful and convenient use for the detection reagent or the reagent kit.

Furthermore, the presence or absence of the pathogenic bacterium to be detected can be determined with the detection reagent or the reagent kit simply by causing a sample to be inspected to come into contact with a culture container such as, e.g. petri dish, etc. that contains an agar culture medium containing the phage according to the present invention poured therein and allowed to stand at an appropriate place and temperature for a selected period of time long enough to allow the detection of the propagated pathogenic bacterium. Therefore, it is very convenient and useful to use the detection reagent or the reagent kit according to the present invention for identifying pathogenic bacterium to be detected. In addition, the detection reagent or the reagent kit according to the present invention can be employed in a very simple way because it does not require any other special instruments or apparatus for determination. The detection reagent or the reagent kit according to the present invention can easily be employed, for instance, as a first screening for pathogenic bacterium.

The bio-bactericidal material according to the present invention has a variety of applications. Further, the bio-bactericidal material according to the present invention can be applied to anything including, e.g. any place where the pathogenic bacterium may exist and any article which might be infected with the pathogenic bacterium. It can be used to control the infection of such an article or the like with the pathogenic bacterium, or to inspect whether such a thing or place is contaminated with the pathogenic bacterium.

More specifically, the bio-bactericidal material according to the present invention may be applied directly to, e.g. food, including fresh food, for instance, by spraying directly on the food therewith or immersing it therein or washing it therewith. Therefore, the bio-bactericidal material can be used, for instance, so as for the food, such as fresh food, or any other things to fail to be contaminated by the pathogenic bacterium at any stage of storing or cooking the food.

Further, the novel bio-bactericidal material according to the present invention can prevent the contamination of places and articles, etc. by the pathogenic bacterium, for instance, by directly spraying in the places such as, e.g., pantries, kitchens, storage room, etc. with it, which must be kept clean and free from germs, or the articles including, for example, clothing articles, such as, e.g., aprons, white overalls, etc. Moreover, the novel bio-bactericidal material according to the present invention can also be used as a washing liquid in order to prevent contamination of the pathogenic bacterium through the invasion into the human body via the hands, etc.

In addition, the novel bio-bactericidal material according to the present invention can also be employed, for instance, in the cultivation and preparation of fresh food and the like. More specifically, for instance, it may be applied by spraying on food including fresh food etc. with it, adding it to a medium for cultivating vegetables such as radish shoots, etc., spraying on cultivated vegetables such as radish shoots, etc. with it, or adding it to the water used particularly for cultivating vegetables in water, etc.

Furthermore, the novel bio-bactericidal material according to the present invention can be employed for the disinfection of the places, for example, where fresh food is to be processed, such as fish markets, meat processing facilities, etc. and livestock breeding farms such as cowhouses or the like.

The present invention will be described in more detail by way of example. It is to be understood herein, however, that the examples are described hereinafter for illustrative purposes only and they should not be construed as limiting the present invention in any respect and that any modifications and variations not departing from the scope and spirit of the invention are encompassed within the scope of the present invention.

EXAMPLES

Example 1

Screening of Bacteriophage

Samples were collected from the excrements of pigeons, crows, cattle, dogs, cats, and chickens and from sewage. Each sample was dissolved into 1 gram for each of the excrements and 5 or 10 ml for the sewage in an LB culture liquid and centrifuged to separate the supernatant from the residue. To the resulting supernatant were added host *E. coli* K, B and C strains, which each contained restriction enzyme minus (r−) and modification enzyme positive (m+), in order to allow them to be infected with a phage which might be present in a small number in the supernatant of the sample, and with the purpose of amplifying the phage. The lytic solution was then plated with *E. coli* O-157 to isolate a single plaque, followed by carrying out plural stages of amplification to yield a high titer stock. A substantially completely lytic and clear plaque was selected therefrom and then allowed to be in contact with 5–10 mM EDTA at high temperatures (55° C.–65° C.) for several hours to select only a naturally occurring phage which contained a deleted DNA. Only the phage which had stable and essential genes only was selected by repeating this operation several times.

A number of phages were separated by carrying out the screening in the manner as described above and investigated for their action against plural kinds of intestinal hemolytic *E. coli* O-157. As a result, four kinds of bacteriophages were selected having a strong action against intestinal hemolytic *E. coli* O-157, and these were coded as bacteriophages #1, #2, #3 and #4, respectively. These phages were determined by the DNA sequences of their fragments in a manner which will be described hereinafter.

Example 2

Isolation of Bacteriophage

The *E. coli* was incubated in an L-broth culture medium containing polypeptone, yeast extract and so on contained in a 1 liter-volume jar fermentor at the stage where absorbency reached 0.2 (amounting to the number of cells of *E. coli* of $2–3\times10^8$ per ml). The phage capable of destroying only intestinal hemolytic *E. coli* O-157 separated by screening in Example 1 was added to the culture medium so as to reach MOI=20 (as described in Japanese Patent Application No. 8-261,132), followed by incubation at 37° C. for 4 hours or longer. When the culture liquid became somewhat transparent, several drops of chloroform were added and the culture liquid was further incubated at 37° C. for another 10 minutes, followed by centrifugation at 8,000 rpm for 30 minutes to separate the supernatant from the residue. The resulting supernatant was then filtered aseptically with a 0.45 micron millipore filter to separate the phage that can eat and destroy only specific intestinal hemolytic *E. coli* O-157 and the resulting phage was then stored at 4° C.

Example 3

Preparation of the Novel Phage Storing Liquid (1) A novel phage storing liquid was prepared by adding glycine in the amount of 15 grams, $CaCl_2$ $H_2O$ at the rate of 0.5 mM, NaCl at the rate of 0.5%, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(2) A novel phage storing liquid was prepared by adding glycine in the amount of 15 grams, NaCl at the rate of 0.5 mM, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(3) A novel phage storing liquid was prepared by adding glycine in the amount of 15 grams, $CaCl_2$ $H_2O$ at the rate of 0.5 mM, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(4) A novel phage storing liquid was prepared by adding glycine in the amount of 15 grams, $CaCl_2$ $H_2O$ at the rate of 0.5 mM, and NaCl at the rate of 0.5% and adjusting the pH with NaOH to pH6.8 to pH7.0, followed by making the volume of the liquid 1,000 ml with MILI-Q water and fertilizing the liquid at 121° C. for 15 minutes in autoclave.

(5) A novel phage storing liquid was prepared by adding $CaCl_2$ $H_2O$ at the rate of 0.5 mM, NaCl at the rate of 0.5%, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(6) A novel phage storing liquid was prepared by adding glycine in the amount of 7.5 grams, $CaCl_2$ $H_2O$ at the rate of 0.5 mM, NaCl at the rate of 0.5%, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(7) A novel phage storing liquid was prepared by adding arginine at the rate of 0.2M, $CaCl_2$ $H_2O$ at the rate of 0.5 mM, NaCl at the rate of 0.5%, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

(8) A novel phage storing liquid was prepared by adding lysine at the rate of 0.2M, $CaCl_2$ $H_2O$ at the rate of 0.5 mM, NaCl at the rate of 0.5%, and glycerol at the rate of 0.02% and adjusting the pH with NaOH to pH6.8 to pH7.0, followed by making the volume of the liquid 1,000 ml with MILI-Q water and fertilizing the liquid at 121° C. for 15 minutes in autoclave.

Example 4

Preparation of a Novel Bio-bactericidal Material

The bacteriophage separated in Example 1 was propagated by using the host of *E. coli* by conventional processes so as to propagate the number of the bacteriophages at about 100 times for each step. More particularly, *E. coli* in a logarithmic growth phase was infected with the bacteriophage at MOI=10 and chloroform was added at about 100 minutes after the *E. coli* was lyzed. Thereafter, the remaining (DNA, RNA, protein, cell walls, etc.) of the *E. coli* was removed by centrifugation, yielding a crude material of the bacteriophage, which was found to have an infective ability in the concentration of about $10^9$ per ml.

To the resulting crude material of the bacteriophage were then added glycerol at the rate of 0.1% to 0.01% and a salt such as, e.g., lauroyl sarcosine salt, benzoic acid salt, etc., as a stabilizer, as well as Mg, Mn or Ca as a metal, thereby yielding the novel bio-bactericidal material according to the present invention. It was found that a titer of the bacteriophage was not inactivated and kept stable when the resulting bio-bactericidal material was stored in a chamber at low temperature (4° C.±1° C.) for 6 months. In this example, the bio-bactericidal material was prepared basically by mixing two different kinds of bacteriophages in order to cause no occurrence of the remaining resistant bacteria. For instance, when a mixture of phage T2 with phage λ was used, it was found that the frequency of occurrence of resistant bacteria was as low as $10^{-6}\times10^{-6}=10^{-12}$ and that this frequency can be said to cause no theoretical or experimental problems. From this, hazardous bacteria, including pathogenic bacteria, can be combated against completely by the use of the bio-bactericidal material prepared in this example. Moreover, the bio-bactericidal material was able to prevent a decrease in the disinfection ability even when it was used frequently.

Example 5

Preparation of a Novel Bio-bactericidal Material

The bacteriophage separated in Example 1 was propagated using a host of *E. coli* by conventional processes so as to propagate the number of the bacteriophages at about 100 times for each step. More particularly, *E. coli* in a logarithmic growth phase was infected with the bacteriophage at MOI=10 and chloroform was added at about 100 minutes after the *E. coli* was lyzed. Thereafter, the remaining (DNA, RNA, protein, cell walls, etc.) of the *E. coli* was removed by centrifugation, yielding the supernatant containing the bacteriophage. The resulting supernatant was further purified by precipitation with polyethylene glycol and density ingredient centrifugation with CsCI, thereby yielding a product of the bacteriophage which was found to have the infective ability in the concentration of about $10^{12}$ per ml.

To the resulting product of the bacteriophage were then added glycerol at the rate of 0.1% to 0.01% and a salt such as, e.g., lauroyl sarcosine salt, benzoic acid salt, etc., as a stabilizer, as well as Mg, Mn or Ca as a metal, thereby yielding the novel bio-bactericidal material according to the present invention. It was found that a titer of the bacteriophage was not inactivated and kept stable when the resulting bio-bactericidal material was stored in a chamber at low temperature (4° C.±1° C.) for 6 months. In this example, the bio-bactericidal material was prepared in substantially the same manner as in Example 1 and the resulting bio-bactericidal material was found to have substantially the same action as the bio-bactericidal material prepared in Example 1.

The bio-bactericidal material was applied to bacteria at an appropriate dilution rate to reach MOI =10 in order to comply with the usage. Further, the operations as described above were carried out in principle in a chamber at low temperature (4° C.±1° C.) and the bio-bactericidal material of this example was stored usually in a chamber of low temperature (4° C.±1° C.).

Example 6

Preparation of a Novel Bio-bactericidal Material

*E. coli* was added to an L-broth culture medium comprising 10 grams of polypeptone, 3 grams of yeast extract and 12.5 grams of NaCl, and the culture medium was incubated at 37° C. in a jar fermentor. At the stage when the OD reached 0.2, when measured by spectrophotometer, the bacteriophage was added (MOI=20). The number of cells of *E. coli* at this stage were found to be about 2–3×$10^8$ per ml.

After additing the bacteriophage, the culture liquid medium was incubated at 37° C. for 4 hours in the jar fermentor while air was being fed inside. As the culture liquid medium became somewhat transparent, several drops of chloroform were added, followed by centrifugation at 8,000 rpm for 30 minutes to remove the residue of the medium and separating the supernatant therefrom. The resulting supernatant was employed as a mother liquid for the preparation of the bio-bactericidal material.

Example 7

(1) Detection Kit for Detecting Pathogenic Bacteria

A 10% agar culture medium containing the following composition was warmed to 45° C. and dissolved completely, followed by pouring the medium as a lower layer of the culture medium into a petri dish and allowing it to stand at room temperature and to solidify.

The composition of the agar culture medium was as follows:

10 grams of polypeptone;

3 grams of yeast extract;

2.5 grams of NaCl;

0.1% of Glucose, and 5 mM of $CaCl_2$.

Separately, a 5% agar culture medium having the same composition was prepared and 0.1 ml of a solution containing intestinal hemolytic *E. coli* O-157:H7 strain in the concentration of $4\times10^7$ per 0.2 ml was added to 3 ml of the 5% agar culture medium as prepared above. The resulting culture medium was heated to 45° C. and dissolved completely, followed by pouring it uniformly on top of the lower layer of the culture medium, and allowing it to stand at room temperature to solidify, thereby forming an upper layer of the culture medium and yielding a two-layer agar culture medium.

A solution containing the bacteriophage in the amount of 0.1 ml was streaked on the surface of the upper layer of the culture medium and the resulting culture medium was incubated at 37° C. for 7 hours to grow intestinal hemolytic *E. coli* O-1 57:H strain, followed by counting the number of plaques formed by the phagocytic action of the phage and calculating the number of the phages. It was found as a result that, if the objective phage was present in the sample, the plaque was formed in the agar culture medium in the number corresponding to the number of the phages and the objective phage was detected.

(2) Detection Kit for Detecting Pathogenic *E. coli*

An agar culture medium was prepared by the composition as follows:

10 grams of polypeptone;

3 grams of yeast extract;

2.5 grams of NaCl;

0.1% of Glucose, and 5 mM of $CaCl_2$.

To 0.1 ml of a solution containing a mixture of intestinal hemolytic *E. coli* O-157:H strain (number of cells: $4\times10^7$ per 0.2 ml) with phages in a given concentration was added 3 ml of a 5% agar culture medium having the same composition. The resulting culture medium was heated at 45° C., dissolved completely, and then poured uniformly into a petri dish as an upper layer in substantially the same manner as above. The resulting culture medium was then incubated at 37° C. for 7 hours to grow the intestinal hemolytic *E. coli* O-157:H strain to determine the growth inhibitory rate due to the phagocytic action of the phage. Further, when the phage in a low concentration was employed, the number of the phages formed by the phagocytic action of the specific phages was counted to calculate the number of the phages.

As a result, it was found that the intestinal hemolytic *E. coli* O-157:H strain was detected by taking advantage of the phagocytic action of the specific phage. Further, the number (strength) of the phages could be inspected.

The following table indicates the results obtained above. In this case, the strength of the mother liquid was $4.0\times10^{10}$ per ml.

| Dilution of phage solution | Number of plaques (on petri dish) | Strength (calculated) Number of phages |
|---|---|---|
| Mother liquid | Whole area lyzed | Could not be calculated |
| $10^3$ -fold Dilution | Whole area lyzed | Could not be calculated |
| $10^7$ -fold Dilution | Whole area lyzed | Could not be calculated |
| $10^8$ -fold Dilution | 196 | $3.92\times10^{10}$ per ml |
| $10^9$ -fold Dilution | 21 | $4.2\times10^{10}$ per ml |
| $10^{10}$ -fold Dilution | 2 | $4.0\times10^{10}$ per ml |

* Calculation: number of plaques × dilution/0.1 ml (Method for Inspection of Strength of Phage)

*E. coli* was propagated to the absorbency of 0.2, and was mixed with a dilution of phages. The mixture was then coated on an agar culture medium and inspected for the strength of the phage.

Further, the action of the bacteriophage and the bio-bactericidal material according to the present invention will be described.

(Bactericidal Effects on Solid Culture Medium)

The bactericidal action of the bio-bactericidal material according to the present invention was tested by taking into account the case where a pathogenic bacterium as a hazardous bacterium is attached or propagated on a solid material.

As shown in FIG. 1, *E. coli* was coated lengthwise in one streak on the culture medium. Before or after coating, $10^{-1}$-fold, $10^{-2}$-fold, and $10^{-3}$-fold dilutions of the bio-bactericidal material prepared in Example 1 were coated longitudinally on the culture medium. (This method is called the cross-streak method.) The culture medium was then incubated overnight at 37° C. and it was found that all the bacteria in contact with the bacteriophages had been completely lyzed. As a result, no colony was formed and the strong action of the bio-bactericidal material according to the present invention was confirmed.

(Bactericidal Effects in Liquid Culture Medium)

Food (soup, stock, etc.) or bean sprouts, radish shoots, etc. which were prepared or grown in a water culture may sometimes be contaminated with bacteria which may cause food poisoning. However, the bio-bactericidal material according to the present invention can effectively be applied thereto when the concentration of cells of bacteria per unit volume is low. The following experiment was carried out in order to confirm the bactericidal effects of the bio-bactericidal material.

*E. coli* was added to a commercially available culture medium for use in a water culture and bouillon medium was added thereto at the rate of approximately 10% in order to propagate *E. coli* cells. After several hours, the culture medium was started incubating at 37° C. and the bio-bactericidal material was added. As a result, it was found that all the bacteria were completely killed in 12 hours.

Even when hazardous bacteria were grown, it was found that they could be killed completely by applying the bio-bactericidal material according to the present invention at MOI=10–50.

(Bactericidal Effects by Spraying)

The effects of the bio-bactericidal material according to the present invention upon a chopping board used at a house kitchen for about 1 year were also investigated. First, 10 thousand cells of *E. coli* were added to about 10 ml of a culture medium (bouillon medium) and the resulting solution was coated over the entire area of the front and back surfaces of the chopping board, followed by the removal of excess liquid 30 minutes after coating. The chopping board was then divided into two sections and one section was coated with the bio-bactericidal material according to the present invention as a test sample, while the other was used as a control. The test sample was sprayed over the entire area with the bio-bactericidal material according to the present invention. On the other hand, the control was sprayed with an equal amount of water in place of the bio-bactericidal material. The test sample and the control were placed overnight at 37° C. The number of remaining bacteria was calculated by washing the chopping board divisions with 500 ml of the medium and counting the number of the bacteria. It was found as a result that no bacterium was detected from the test sample while about 1 to 2 million bacteria were detected on the control sample.

(Effects Upon *E. coli* Attached on Meat)

Ten beef steaks were each sprayed with *E. coli* in the number enough to form an average of 100 colonies. Ten beef steaks were divided into two groups, one as a test and the other as a control. The beef steaks of the test group were each sprayed over the entire area with the bio-bactericidal material according to the present invention. The beef steaks of the control group were kept as they were without spraying. About ten cubes were cut in a random manner from each of the steaks and replicated on an agar culture medium, followed by incubating it overnight to count the number of colonies which may be formed when the bacteria were alive and grew. As a result, it was found that no colony was formed on the beef steaks of the test group which was sprayed with the bio-bactericidal material according to the present invention, while 100±10 colonies were formed for the beef steaks of the control group which was not sprayed with the bio-bactericidal material. These results indicate that the bio-bactericidal material according to the present invention demonstrated high bactericidal effects.

(Method of Determination of Base Sequences of Bacteriophage)

The base sequences of DNA fragments of bacteriophages #1, 190 2, #3 and #4 were obtained by screening in the manner as described above among the bacteriophages according to the present invention were determined in a conventional way.

(1) Multiplication of Bacteriophages

An L-broth liquid culture medium was infected with *E. coli* N60 and incubated until the value of OD reached 0.2 when measured by spectrophotometer. At this stage, the bacteriophage was added theoretically to the amount of MOI=10 and the culture medium was placed on ice for 30 minutes, followed by stirring the medium at 37° C. for about 20 hours. Thereafter, one drop of chloroform was added thereto and the medium was stirred for another 5 minutes. The resulting culture medium was then centrifuged at 4,500 rpm for 20 minutes at 4° C. to separate the supernatant from the residue and the resulting supernatant was then transferred to a sterilized bottle. The supernatant was then sprayed onto an L-broth agar medium to measure the concentration of the bacteriophage. As a result, it was found that the culture liquid in the amount of 500 ml contained the bacteriophages in the concentration of $1\times10^{10}$ per ml.

(2) Concentration of the Bacteriophage Liquid

To the culture liquid containing the bacteriophages was added a mixture of 20% PEG with 2M NaCl and the liquid was allowed to stand on ice for 30 minutes, followed by centrifugation at 12,000 rpm for 20 minutes at 4° C. and removal of water from the liquid. To the precipitated material was added 1 ml of a SM solution to form a suspension which in turn was stirred well and transferred to a microcentrifuge tube. The bacteriophage in the tube was then sprayed onto an L-broth agar medium to measure the concentration of the bacteriophage and it was found that the concentration of the bacteriophage was at $1.3\times10^{20}$ per ml.

(3) Preparation of Phage DNA

To the concentrated culture liquid were added 10% SDS and 0.5M EDTA so as each to amount to 0.1% and 5 mM (each a 1/100 amount), respectively, and the resulting liquid was then heated at 68° C. for 15 minutes. Thereafter, the liquid was extracted with phenol and then with a phenol-chloroform mixture, followed by extraction with chloroform. The resulting aqueous phase was combined with an equal amount of isopropanol and the resulting solution was allowed to stand at −70° C. for 10 minutes. Thereafter, the solution was centrifuged at 15,000 rpm for 15 minutes at 4° C. and the resulting supernatant was removed. The residue was then washed with ethanol and dried by suction to yield a dry material which in turn was dissolved in 1 ml of a TE solution.

(4) Gel-electrophoresis

To 4 μl of the resulting DNA solution were added 2 μl of 1M buffer, 13 μl of sterilized water, and 1 μl of restriction enzyme Hind III, and the mixture was stirred at 37° C. for 1 hour. To the mixture was added a 1/10 volume of a reagent for the superimposition of a sample and subjected to gel-electrophoresis using a 0.7% agarose gel at 100 V for 2 hours. The resulting agarose gel was then allowed to stand for 2 hours in a solution in which 20 μl of ethidium bromide was dissolved in 400 ml of a TAE solution and the bands were then confirmed with a UV lamp.

(5) De-phosphorization of Vector-plasmid DNA

Then, 3 μl of plasmid (pkk223), 2 μl of 1M buffer, 14 μl of sterilized water, and 1 μl of restriction enzyme Hind III were added, and the resulting mixture was stirred for 1 hour at 37° C. The mixture was then allowed to stand for 15 minutes in a water bath at 70° C. so as to deactivate the restriction enzyme Hind III. In order to carry out de-phosphorization, 2 μl of buffer, 0.5 μl of BAP, and 26.5 μl of sterilized water were added to 18 μl of the vector, and the resulting mixture was stirred for 2 hours at 37° C. Thereafter, the mixture was extracted twice with a phenol-chloroform mixture and allowed to precipitate with ethanol, followed by dissolving the precipitated material in 80 μl of a TE solution. In order to determine the presence or absence of the vector, a 1/10 volume of a reagent for superimposition of a sample was added to the resulting solution. This in turn was subjected to gel-electrophoresis using a 0.7% agarose gel at 100 V for 2 hours. As a result, the presence of the vector was confirmed.

(6) Inactivation of Enzyme

In order to carry out a ligase reaction, 2 μl of 1M buffer, 13 μl of sterilized water, and 1 μl of restriction enzyme Hind III were added to 4 μl of the aqueous phage DNA solution. The resulting mixture was then stirred for 1 hour at 37° C., followed by allowing the mixture to stand in a water bath at 70° C. for 15 minutes to inactivate the restriction enzyme Hind III.

(7) Ligase Reaction

A mixture of the resulting aqueous phage DNA solution with the vector de-phosphorized in the manner as described above was allowed to stand in a water bath for 10 minutes at 60° C. As (1) a phage DNA cut with Hind III; (2) a phage DNA cut with Hind III and a vector de-phosphorized; (3) a vector de-phosphorized; and (4) a vector cut with Hind III, there were each added 10 μl of 10× buffer and 10 μl of an aqueous DNA solution, followed by addition of sterilized water so as to make the total volume 100 μl and by the addition of 2 μl of *E. coli* DNA ligase. The resulting mixture was then allowed to stand overnight at 16° C.

(8) Transformation

To 50 $\mu$l of the competent cell (HB 101) were added 5 $\mu$l of each of the samples (1), (2), (3) and (4) above. The resulting mixture was allowed to stand on ice for 30 minutes, followed by allowing the mixture to stand at 42° C. for 45 seconds and then on ice again for 2 minutes. Thereafter, an L-broth liquid medium was added in order for the entire volume to amount to 0.5 ml. The resulting mixture was stirred for 1 hour at 37° C., followed by the addition of ampicillin thereto and spraying the mixture onto an L-broth agar medium.

(9) Culture of Recombinant Clone

The colony of the vector (2) above was added to 500 ml of an L-broth liquid medium with ampicillin added. The resulting mixture was incubated for about 24 hours. The culture medium was then centrifugated at 6,000 rpm for 15 minutes at 4° C., and the resulting supernatant was removed.

(10) Purification of Plasmid

A plasmid with the phage DNA was then purified with a plasmid purification kit (product by Funakoshi K. K.). First, 10 ml of P1 and 10 ml of P2 were added to a pellet. The pellet was then stirred slowly, and allowed to stand at room temperature for 5 minutes. Thereafter, 10 ml of cooled P3 was added, and the resulting mixture was stirred slowly and allowed to stand on ice for 20 minutes. The mixture was then centrifuged at 20,000 rpm for 30 minutes at 4° C. to separate the supernatant from the solid material. Only the resulting supernatant was further centrifuged at 20,000 rpm for 30 minutes at 4° C. The resulting supernatant was added to a column washed with 10 ml of QBT. The column was then washed twice with 30 ml of QC, and the resulting supernatant was purified with 15 ml of QF. To the resulting purified liquid was added a 0.7 volume of isopropanol, and the mixture was centrifuged at 15,000 rpm and 4° C. for 30 minutes and the resulting precipitated residue was washed with 70% ethanol, followed by drying it for 5 minutes and dissolving it in 1 ml of sterilized water. The resulting plasmid was cut with Hind III and subjected to gel-electrophoresis.

The resulting fragments were subjected to conventional procedures for analyzing the base sequences. As a result, it was confirmed that the bacteriophages #1, #2, #3 and #4 had DNA fragments which contained the partial base sequences as indicated, respectively, by SEQ ID NOS 1–4, SEQ ID NOS 5–14, SEQ ID NOS 15–19, and SEQ ID NOS 20–24.

INDUSTRIAL UTILIZABILITY

The present invention provides a highly specific bacteriophage which can attack a certain specific kind of a pathogenic bacterium so that the bacteriophage according to the present invention is extremely useful because it can be applied to food such as, e.g., fresh food, etc., and used in places or applied to, e.g., tools for storing, cooking or processing such food. It can even be sprayed on persons handling such food and tools as well as working at such places, etc., in order to effectively prevent infection from the pathogenic bacterium. It can be applied readily in a wide variety of fields in the manner as described above. Further, the bacteriophage according to the present invention can be applied as a disinfectant for the infected places, good and the like which are suspected to be infected with the pathogenic bacteria, and kill the pathogenic bacteria causing infection readily and certainly in a short time. Therefore, the bacteriophage according to the present invention is extremely useful for disinfection of the pathogenic bacterium. At the same time, use of the bacteriophage enables the detection of the pathogenic bacterium as a host bacterium with ease and certainty in an extremely short period of time. Moreover, it offers a great advantage in that it can readily and surely determine the presence or absence of infection and sources of infection, etc. in a very short period of time. As a consequence, the prevention and treatment of infection can also be conducted rapidly.

Further, the present invention provides a bacteriophage which has a high level of specificity to a certain kind of the pathogenic bacterium including, for example, pathogenic *E. coli* such as, e.g., intestinal hemolytic *E. coli,* etc. The such bacteriophage can be applied to food, such as fresh food, and to places and tools for storing, cooking or processing food, etc. as well as to persons handling food, etc. to thereby completely prevent the infection particularly with the pathogenic *E. coli* including, e.g., intestinal hemolytic *E. coli.* Furthermore, the bacteriophage according to the present invention can be used for the disinfection of places and tools as well as to even persons when they are infected with or are suspected to be infected with the pathogenic *E. coli.* It can kill the pathogenic *E. coli* with high degree of certainty and readiness in a very short period of time. In this respect, too, the bacteriophage according to the present invention is extremely useful. In addition, the bacteriophage according to the present invention is also very useful because it can surely detect pathogenic *E. coli* in a very simple way and in a very short time of time. The presence or absence of infection, the source of infection and the like can also be determined readily for sure within short.

Furthermore, the present invention can provide a novel bacteriophage so that different kinds of pathogenic bacteria acting as host bacteria can be increased, thereby enabling the competition with increased kinds of pathogenic bacteria and applying it to a wider variety of fields in terms of prevention and treatment of infection.

Moreover, the present invention allows two or more different kinds of phages to be employed concurrently as a cocktail, in addition to the use of a single kind of highly specific bacteriophage particularly for a pathogenic bacterium. Therefore, it is very convenient and useful that the bacteriophage can be applied in the form of a cocktail because the application of the cocktail can concurrently compete with the different kinds of pathogenic bacteria.

The present invention further provides a screening method for finding the novel bacteriophage and the screening method can offer advantages in that the novel phages extremely specific to pathogenic bacteria can be singled out with certainty and ease.

The present invention furthermore provides the novel bio-bactericidal material which contains the novel bacteriophage and that can attain the above-mentioned effects achieved by the provision of the bacteriophage according to the present invention. More specifically, the bio-bactericidal material containing the novel bacteriophage according to the present invention can be applied, for instance, to food, such as, e.g., fresh food, etc. or to places and tools, etc. for storing, cooking or processing food, or to persons handling food, etc. and it can surely prevent the infection of food, places, tools, etc. and persons from pathogenic bacteria, particularly including, for example, pathogenic *E. coli* such as, e.g., intestinal hemolytic *E. coli,* etc. In addition, it can be applied to food, places, tools, etc. and persons who handle food, etc. which are infected with or suspected to be infected with the pathogenic bacteria including, e.g., pathogenic *E. coli* such as intestinal hemolytic *E. coli,* etc. In each case, the bio-bactericidal material according to the present invention can kill the pathogenic bacteria readily and surely in a short period of time.

In accordance with the present invention, the addition of the stabilizer or storing agent according to the present invention to the novel bio-bactericidal material of the present invention is useful because it can store the novel bio-bactericidal material according to the present invention in a stabilized manner for an extended period of time while sustaining the action of the bacteriophage contained therein.

Further, the novel bio-bactericidal material according to the present invention can contain different kinds of the novel bacteriophages of the present invention so that the such bio-bactericidal material can present the advantages that it can compete with different kinds of the pathogenic bacteria concurrently.

Moreover, the present invention provides a method for the production of novel bacteriophages and the method according to the present invention can produce the bacteriophage at a large scale and at low cost. Therefore, the method of the present invention is very useful particularly in preparing the bio-bactericidal material containing the novel bacteriophage according to the present invention.

Furthermore, a metal ion such as calcium ion, etc. in a culture medium for incubating the bacteriophage is used in the method for the production of the bacteriophage of the present invention, it can assist in the growing of bacteriophages which require a metal ion and offer an advantage in that the growth of the such phage is promoted.

In addition, the present invention provides a stabilizer or storage agent capable of maintaining the novel bacteriophage of the present invention in a stable manner and the stabilizer or storage agent according to the present invention can keep the novel bacteriophage in a stable way for a long period of time. Therefore, the novel bacteriophage according to the present invention prepared by the addition of the storing liquid can offer great advantages in that the bacteriophage can be stored in a stable manner for an extended period of time.

Moreover, the present invention provides a detection method for detecting pathogenic bacteria and a reagent kit for detecting pathogenic bacteria. The detection method and the reagent kit according to the present invention is very useful because they can detect pathogenic bacterium as a host bacterium readily and surely in a short period of time, taking advantage of the action of the bacteriophage. Further, the detection method and the reagent kit according to the present invention offer a great advantage in that a sample can be inspected for the presence of pathogenic bacteria on site, and even in emergency situations where infection from pathogenic bacteria is suspected. Also, the present invention is very useful because the inspection of the sample can be conducted in a simple and sure way in a short period of time, taking advantage of the reagent kit of the present invention alone, i.e., without using any measurement instruments or anything else for detection. Furthermore, the detection method according to the present invention is a highly sensitive method that can detect the pathogenic bacterium even if the concentration of the pathogenic bacterium is very low because the phage can eat up the host bacterium and propagates even if only one cell of the bacterium exists in a sample.

Also, the reagent kit of the present invention for use in the detection method for the detection of the pathogenic bacterium is of a very simplified configuration, for instance, which consists of a typical container such as, e.g., a petri dish, etc., and has an agar culture medium that contains therein together with the bacteriophage of the present invention. Therefore, the reagent kit according to the present invention can provide a great advantage in that it can detect the objective pathogenic bacterium without using any measurement instruments or other materials, simply by placing the reagent kit in a place where bacteria are likely to grow in a short period of time, i.e. in a period of time long enough to allow the phage to eat up the bacteria.

What is claimed is:

1. A bacteriophage having specificity to pathogenic *Escherichia coli* O-157 and having a DNA containing a fragment with a base sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

2. A bio-bactericidal material comprising a bacteriophage having specificity to pathogenic *Escherichia coli* O-157 and having a DNA containing a fragment with a base sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, :SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

* * * * *

SEQUENCE LISTING

<160> NUMBER OF SEQ ID NOS: 24

<210> SEQ ID NO 1
<211> LENGTH: 628
<212> TYPE: DNA
<213> ORGANISM: Bacteriophage

<400> SEQUENCE: 1
tcatcatccc atacttcttc agtactatat tcagcactgt gaagttggtg ttcaggaatg 60
aaatcaggaa tttgcatttc acgttctttt tcttggatta gttcttcacg ggttttaatg 120
accgtaccac ctgaaccaat cttatcacca cgagcattta ggtttgcatt acctagtgct 180
acttggtgct ggttttgata ctttagcata tccatatcaa ttgttgttcc acgataagtt 240
gtgtgttttg acatataaaa atcctttttc tatgtgagtg atataacgcc tcaaacaaca 300
ttatatcaca tgtttttcta ccatttcaaa aattcattta catctagttt atacttcaaa 360
gaatcaacca tatgcaaatc aatcaggaac aaacaatacg aagccactga actaccacgc 420
ccaagacccc aaaaaatatt gtgctcttcc atataatcaa ctaaccagat catacatctt 480
aaaagcttgg ctgttttggc ggatgagaga agattttcag cctgatacag attaaatcag 540
aacgcagaag cggtctgata aaacagaatt tgcctggcgg cagtagcgcg gtggtcccac 600
ctgaccccat gccgaactca gaagtgaa 628

<210> SEQ ID NO 2
<211> LENGTH: 780
<212> TYPE: DNA
<213> ORGANISM: Bacteriophage -continued

```
<220> FEATURE:
<223> OTHER INFORMATION: "n" at various positions throughout the
      sequence may be a, t, g, c other or unknown

<400> SEQUENCE: 2

ttcagttaaa caatattgtg agactacgtg ctgctggtat tgaagatgca cgtttagaat    60

aactatccat aaggncgcat tacgcgtctt tttctatgcg agaataaaat gacaaaatta   120

gatgagttcc tatcaaacgt atcagtacta gacaccgaaa caactggtgt cgaaagtgaa   180

gatgatatta ttgaatttag tatttcatat cctcacgatg cacatgagaa tattgatact   240

attgataact acactttgcg ttataaacca ctaaaagata taccaccaga agcaagtgct   300

gtgcatttta tcagtactga agatgtagca aactgcattg gttataaaga tgacttagaa   360

aacattgacg cactaatggg gtgtcgtaat tattttattg gacacaacgt tcaatttgac   420

cgccgaatga tggtagataa cgaatataaa tatcgtaact cagtttcgca gtacttgctc   480

gatgaagata aatggatttg tacccttcgt ttagctaaga agatgtttgc agaagacact   540

gaatttaaaa acttaactct aagttatttg tggtataaat ttggttgcta tcgtgatgta   600

catcgtgcag tcaatgctca cgcagcaaaa gatgacgtgt ttatgtgtta tcaagttcta   660

atcaaattga ttgaagttgc gattgaacgt ggacatattg accctaatgg tgacattggt   720

gaacaaatcg taacattctg taatacacca atgcgttata aattcatgcc atttggtaaa   780


<210> SEQ ID NO 3
<211> LENGTH: 518
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 3

aaagatagtg gatgtattat tctcgaaaat ggttctgacg ttgttactga tgacttcagt    60

gtagcgtttg atgtttcacc tgatggttcg ctatcaatgc cacgcttagg gactggtgac   120

atgactgtgt gggtaggttt cactatgggg aatgtaccag gcacggtgta tgtagatgat   180

gctgagttga aagaaagctt ggctgttttg gcggatgaga gaagattttc agcctgatac   240

agattaaatc agaacgcaga agcggtctga taaaacagaa tttgcctggc ggcagtagcg   300

cggtggtccc acctgacccc atgccgaact cagaagtgaa agnccgtagc gccgatggta   360

gtgtggggtc tccccatgcg agagtaggga actgccaggc atcaaataaa acgaaaggct   420

cagtcgaaag actgagcctt tcgttttatc tgttgtttgt cggtgaacgc tctcctgagt   480

aggacaaatc cgccgggagc ggatttgaac gttgcgaa                           518


<210> SEQ ID NO 4
<211> LENGTH: 599
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 4

aagcttcaac aagttcttta aatggaacca ttggagcttc tttcttatct ttatcagtca    60

ggcttgacag catctgtgca aatgttggaa caaaaatttt acccaacttc atagacatct   120

taataccatc tcttgcccca agcagaacga tatttacttt cttaccatta attactctag   180

attctgtttt cattgtgatt ccttaatact ttaaaagaaa caaaaaaggg gaagaccttt   240
```

```
taaagtctcc cccttatagg atttattaaa cacttgacgc tggaattgta gaagtgtagt    300

ctaacttctc acaaccaaaa atccaagttt tagagttctg gtcacgacca agttcaatct    360

gtggtaattc ctgcaaccaa gcattaatac cagttgccag aacagagcct gatgggtcgt    420

agattacgaa gtagaagaga tatcttcttc aagttccata ttgtcttgtt tagcttgaat    480

tgcagaaann ancttgttan gaganagagn ctggattann tcaatctcaa taagacctgg    540

cnttgctcna tttctttgca nggaacctgg ccaccttnac ctacaactgg gngcacaat     599
```

```
<210> SEQ ID NO 5
<211> LENGTH: 585
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 5

ggatccgatt gattaagaca cctgtaccaa tttttggatt tccttctata gaagagttca     60

aagtttatct tgacaaaaac ttctacaatg agcagcctgt tactttgctg aagagtgact    120

tatcagagct tcttgatatg gttatcaagg caacttctga gaaggaacct gagcagaaag    180

ctgagaagaa gactagtaag aagtccgata agaagactga aaagcctgag tagtaacttg    240

aggggttnct tgatagcccc tttatagaac ttagaaggta gcgaaatgaa agagcttata    300

ggtnaagagc ttgacattgt tgatgcnaag acacagagat atatatctac tgttaaattt    360

cttggaatga atgatgcgag tnatgcttac cctctcnact gcntantnct agacaaattt    420

gaggtttgtg gtnttgattt taatgatgat aactttataa gctttgataa ggacggtttc    480

tggcgtggtn agantcatcc tcnagcaaat gaatttgata tgcgcctagt gataccacaa    540

aaaggtnatc cacnaaacgt aaaagatatc cttgttngaa gccta                    585
```

```
<210> SEQ ID NO 6
<211> LENGTH: 578
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 6

ggatccgatc aagngatggt attaagatgt ctatgaagtt gggtaaaatt gttgttccaa     60

catttgcaca gatgctgtca agcctgactg ataaagataa gaaagaagct ccaatggttc    120

catttaaaga acttgttgaa gcttgttttg acagaattga agaaatcaac cttgaagaaa    180

tggctaccct gttatttcaa ggggcaactg ttgatgactt cccacttaat attgatacat    240

acttccaagc aaactacggt gaatttattg attacttagc atttgcgctg gaggcaaact    300

tcggaagttt tttcgaagca agcattttca aaagcctaac ttctcagtaa acatgggtna    360

cactctacag acaccactga ctgatgctgc tgtnnaggcn acctatgaag aagcngacga    420

natgaaattt gtgcttgcta tttatggtat ggaanggtgt naagaaacac ttgaccaact    480

ctttgctatg acattctctg atttattatc nttgagacaa tttcttgaga ttcagangtc    540

gtatnaagag gaaattgctt acnacgaact tnnaanaa                            578
```

```
<210> SEQ ID NO 7
<211> LENGTH: 598
<212> TYPE: DNA
```

-continued

```
<213> ORGANISM: Bacteriophage
<220> FEATURE:
<223> OTHER INFORMATION: "n" at various positions throughout the
      sequence may be a, t, g, c other or unknown

<400> SEQUENCE: 7

ggatccgatt tcgttacaga cttcatgtac agaacatctg cattgtatta ctatgcaaga     60

gcttggtata aagaccttga caacagtcag caaaagctaa tcaaaagtgc tggtgaattt    120

ctgggaacag tcgtgacaat tggtggtgca gttgctgtag tatcaaaatc agtcaagctc    180

ctaagtggtt tggtcggtgg tggcatcttt ggtaaaatct tacaaagact tggtgttagt    240

gcagcaggta cagcagcagc aggagaagca gccgcagcgg caggtggagt tacagcaacg    300

agaatggcac ttggtactgt tggctctgca ttgatgctaa naagtnctac agacccnaat    360

gctgctaaaa actacagtga agttacactt ccnaaaccat ttgaaaatgc tgttgcnaat    420

attacaaacc cnaaaagacc aatgttcttt gatgaaaatg gtcaactcca gtttgcacag    480

tatactcnag acattgaagg ttacagaaag ttaattgaca atggcctatc taattgggag    540

attatcatgg ataaactatc nacatctatt gataattttg ccaataagtt taaccaga      598


<210> SEQ ID NO 8
<211> LENGTH: 600
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 8

ggatccgaag acgaagctaa gactggcact gtaatcaacg gtgaagaaat tcacgtagtt     60

gttgaccgtg tattcttcag caagctgact aaacacccta agattcgtga tgcctatctt    120

gcacagcaga ccccactggc ttggcaacag attactggtt ctctgagaac tggtggtact    180

gacggcgttc aggctcacat gaacactttc tactacggtg gtgttaagtt tgtccagtac    240

aacggtaagt tcaaagacaa gcgtggtaag gttcatactc tggtgagcat tgatggtgct    300

ggtgcanaag ttggtgtttg acacgctttc cctaacgttt ctatgctggg tgaagcaaac    360

aacatcttcn aagtggctta tggcccatgc cctaagatgg gttacgcnaa tnccttggtc    420

nnggaactgt ttgttttcna ataccaaaaa gaccgtgatg aangtattga cttcgaanct    480

cactcttaca tgctgccata ctgtnctcgt cctcagttgc tggtanacgt tcgttctgac    540

gctnaagacg aataatattc ttaangaagg ttatgaaatg tgttatncag gcgacccacc    600


<210> SEQ ID NO 9
<211> LENGTH: 603
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 9

ggatccgatg ataagattgc agaacttggt cgttttgatg acttcaaaat cttcgtaggt     60

actcgtttcg agacagatgc cttcaaacat ttagaagcag cattactaga ccctgcaaca    120

gcaggttttg cggctaagtg gttaccacga gtcaaaccac gtcataagca gtttgtaaaa    180

cgtttctgca agtttgccaa cttgagtgag aaagagtacc gcacactgtt gtctgcacta    240

tctgatacag ttgagcaaaa aatctctgct aatgagtttg gtaagattga ctacagtaag    300
```

-continued

```
attccttcac ttgctgctgc acgttaccaa aaactgttta accgtnaaga tggagagcgt    360

tacaaagctt acatcgagtc cttatcagaa ggtgagacta agattaacgc tggtgctgtt    420

tacccatacg atgtgattaa atctgtcaag tntggtaatg cngatgttgc taatgagcag    480

tggaaagcac taccaaactg gatngcngaa ggtgaaaaca tcttgtgtat gtctgatgta    540

tccagttcaa tgtcttgggt gaattttggc tccnttactg ctctgggata ttggtgtttc    600

nct                                                                  603
```

<210> SEQ ID NO 10
<211> LENGTH: 601
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 10

```
ggatccgatt tgaaaaagct ttaaagcttg ttatgccgca tttagaatct ggaaagctga     60

ctttagagat gcttaatagg gttattcgga gagcttatga aaattaaaga agtggttcaa    120

aaagcaatgc ttgacaactc aactaaagat gaaatgtaca aagaaatttg tgataagttg    180

aattgttcaa gacatgctgc taaggttctt gtctcgtgtt ttatctggga atgctcagaa    240

gcttatatgc aagcttatat gcaacatgca gtgtttgaaa gttctaactt actaggtgat    300

gtagaagcta gtgagaagct aaaagaacct gaagtgaaaa cagtccctaa agttggtaat    360

acataccctc ttaaagacct cnagactgga aagattattg caaaaggtgt agtagagtct    420

gtctaccatg atggtaaata cttacttaaa atatttgagt ntgacagcca ctatacgcac    480

ttatgtggga ttacattctt agtaacngaa gaagacctta ttaggaacaa tagcaacaag    540

tttgcagtac cagcttacca agttttacga taatggtgtg atagatatgg aaaaagataa    600

c                                                                    601
```

<210> SEQ ID NO 11
<211> LENGTH: 607
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 11

```
ggatccgata acttccacca gatgttaccc aagctcttga gtcagcattt atgaggattt     60

tggtaaagtc cactaagcag aataatttgc ttatctcggt aaatgatatt cacagtattg    120

ttgaaggtgc tttggcagag gtcaatcacg agatttatga gtcttactca acatacagaa    180

attaccgtaa agaggttgct caaaattggg acgaactcta ccagaagact aaagatacac    240

tcttcttagg tgaccgtgaa aatgctaact ttgacagcag tttaatttct acgaaaggtt    300

caattatccg tggttacctg actaaagaaa tctttaaaca gtatcatcta acaccagang    360

aacttgaaac cattgagaaa ggctttatct atatccncga tttgagagac ctgatttttg    420

gtggtattaa ctgttgcctg tttgacattg gtaaagtact aaaaggtggc tttgaaatgt    480

ccggcnttga ntnctgtgaa cctaaatctg ttctgtcagc gttgcaggtt attgggtgac    540

gtaatacttt cagcaactgc ncagcaattt ggtggtttta ctttagcana aattgatnag    600

gtacttg                                                              607
```

-continued

<210> SEQ ID NO 12
<211> LENGTH: 585
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 12

```
ggatccgatc tactttgaag gtgatgtaca catttctaaa aacttgtatg taacagaaga     60

agtacatggt tcagatttta tcagtgacac aactggtgtg agctttaatg aacacacgca    120

ccattattac tggacagacc ctgctggtga ggctgatact acagaggcac aataatgaaa    180

acagactttg cattaaatct aggtggtgac tatgttgcca ctttgggttc agattcantg    240

tatgtggctc atggtgattt aaagattact ggtaaccnaa ttagaattat cccnnaagat    300

aataaagcta ctcacgttgc tcaaagactc catattagat gccttctaag ggctggtgaa    360

gtcttcttta atacatctgc tgggttcccn tatttacaac ttgccnaatt taaacngaaa    420

acttctatct ttgacaatta tatgaaagct taccttgttg aaacaagana tgtgtctaac    480

atctataact attcttcttc natggacaac gctcaaagaa aagtgactgt taattttgat    540

gccactacta cnacngatat tttaacngac attacgccag aagtt                    585
```

<210> SEQ ID NO 13
<211> LENGTH: 607
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 13

```
ggatccgatt taaggtctac acacatcctt atcgttgacg gtaagattgc aaaagaccgt     60

actggagtac ttaaaggtga acgtattgat attctggagt tgctatgaag aaaatgtaca    120

gtctctgggg aagggttggt aaaggttttg actggacact tcttcgttca aacgttaaac    180

gtagtgaatt accagaactc attacccact atttaaaaac atacagagag gtngactatc    240

gtgaacaatn aggttaagan ttgtgtgaaa gcaatggttg cacttggagt aatttttcta    300

tctggctgca acccctctta cgaggacaaa aacgcttctt atagcctccc accagagatg    360

caagattgca aagtctataa gttacatggt gatgccataa gcagagatat tgttgttgtc    420

agatgtccaa actctcaaac aacaacatct tatagttatg ggaaaaatgg tcaatcacac    480

actacggtta ttgagtgagg ttttcacgat ggaagtcctn gtaaactata tctattgtta    540

tgatgttgtt cactccactn caaccgtagc tcaacgtaac ccnatcgtcc cacgaagaan    600

gtgantt                                                              607
```

<210> SEQ ID NO 14
<211> LENGTH: 563
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 14

```
ggatccgatt tttaatggtg tacagacagt tgttacggat aatgaaggtc tgattgttaa     60

aaactctact cagaatagac cattatatat tcgtggtgtg gacactacta atgtatcaag    120

atggtggatt ggtgttggtg gtgttgatac gaatgatgtt accctaaata acagttattc    180
```

```
tggaacccaa ttggttctcg ggaatacaac atcatacatt aacaaaacat tgactattgc    240

tggacaagtt caaccttcag atttctctaa cttagatgct agatacttta cgcaaagtgc    300

tagtgatagt agatacctaa gaatcagaag cactancttc aatgtgggaa acactgataa    360

gtgggctaaa attgccactg ttgtgatgcc acaatcagca tccactgctg ttattgaagt    420

atttggtggg tcaggtttta atattaatac accaaaccaa gcangtaaat gtgaaattgt    480

tctgcgaact tcaaataaca atccaaaggg cttaaatgtt gttgcttgga gaacatcana    540

naacaccatt atcanggata ttg                                            563
```

<210> SEQ ID NO 15
<211> LENGTH: 528
<212> TYPE: DNA
<213> ORGANISM: Bacteriophage

<400> SEQUENCE: 15

```
aagcttgaca atccctgaag aggatatcag agacagtatt gtacaaggta ttaatgccta     60

cggaagaact cttaaggttg gtagtgacgt tatccctaac agaatctacg gatatatcta    120

tgacgtaatt aaaggtattg agattaacga ggttaaagta gccttatcaa acagccaatc    180

agttccacct agtgacggac aatatactac agcaagaatt actgttgacg gtgaccaata    240

tactgtttgg gaaagcagcc agtataccat cactaaggag taacaatgtt tgaaaagatt    300

gatagtgttt attataaaac acttgatgaa agaactgtaa cacagtttaa agataagttt    360

atctatacaa gcatcttgaa agcaatcact gatgagttac aaacattaga ggatgtttgc    420

tggcagatgc acacagagag aaatatcagg acgtcagtag gccaacaact tgataatatt    480

ggctcactga ttaaagttcc taagaccttt aggtgcagat gatgaaac                 528
```

<210> SEQ ID NO 16
<211> LENGTH: 543
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 16

```
gaagatgata aagctactca ggttgctcaa agactccata ttagatgcct tctaagggct     60

ggtgaagtct tctttaatac atctgctggg ttcccatatt tacaacttgc caaatttaaa    120

cagaaaactt ctatctttga caattatatg aaagcttacc ttgttgaaac aagagatgtg    180

tctaacatct ataactattc ttcttcaatg gacaacgctc aaagaaaagt gactgttaat    240

tttgatgcaa ctactacaac agatatttta acagacatta cgcaagaggt taatatctaa    300

tggcaggatt aactacaaca ggattacaaa ctctaagata tcaggaaatt tttgataata    360

tcaaatcaag acttcttaga gatatctcac caaaccttga cgtttctgaa gatagccaat    420

taggtctctt cctagcttca attgcaaggt ctttagcaga tacacatgag attctntcag    480

aaatctatga cggcggggac aattgacaag gctgaaanga tttaaccttg atgatatcac    540

agc                                                                  543
```

<210> SEQ ID NO 17
<211> LENGTH: 557
<212> TYPE: DNA
<213> ORGANISM: Bacteriophage
<220> FEATURE:
<223> OTHER INFORMATION: "n" at various positions throughout the sequence may be a, t, g, c other or unknown

<400> SEQUENCE: 17

```
caatgaagga tgctcgtgca atttgcaatg agttgaatgc aaagattggt aagaaatgca     60

aagactggaa gccagtaaaa acagttaaaa ctgtgaagta ctataacagt catgttgtta    120

accactttga gcttgagtca agtcgctaca caggattgat tgatgcacca tatacaccaa    180

ttgagtttga agtttctcgt atgactcagg tagcagttgt taaagactac ttgaaatcag    240

ttggttggat tccagatgac tggaactaca agaaagattc agacggtcgc cctgtcaaag    300

tttgtcgttt canagacaac aaaaagatga ttacaaagca tcctaagtgg caggagatgg    360

ttgaacggtg tgggttgagt tatgttgaac acgaaagtgt ccagtacatc gaacataact    420

ggtctgtgaa gaagtncacg gatttgcttg aaccttgctt aatccgtact tcccaaaact    480

tactgaatct tcttatgata cgattgaang tgagcttgga cagaagattg ctaaatacta    540

tactttgatg cccgacg                                                   557
```

<210> SEQ ID NO 18
<211> LENGTH: 528
<212> TYPE: DNA
<213> ORGANISM: Bacteriophage
<220> FEATURE:
<223> OTHER INFORMATION: “n” at various positions throughout the
sequence may be
a, t, g, c other or unknown

<400> SEQUENCE: 18

```
aagcttggaa tgagtatgtt gaagcatttg gtcacgcaga tggactgaag agaattacca     60

agtaccctaa gacaaagtat cgtcagcagg tacgtaacgg tgagatgcag acatatgaaa    120

tcaagccatt tggtaagcca actacaaaga tttttaacat tgaaaagaga aattgctata    180

caccaaccaa ctctgtaact ggtgaagagt acaaggaggg ttttgtagca atgaaggatg    240

ctcgtgcaat ttgcaatgag ttgaatgcaa agattggtaa gaaatgcaaa gactgggagc    300

cagtnaaaac agtnaaactg tggaagtact attacaagca aggtgnttac cacttttgag    360

ctttgagtca agtcgctaca caaggattga ttgatgcanc atatacacca attgagtttg    420

aagtttcncc gtatgactca ngtagcaatt gttaaagact acttgaaatc agttgggtgg    480

attccagatg actggaacta caagaaagat tcagacggtc gccctgtc                 528
```

<210> SEQ ID NO 19
<211> LENGTH: 528
<212> TYPE: DNA
<213> ORGANISM: Bacteriophage
<220> FEATURE:
<223> OTHER INFORMATION: “n” at various positions throughout the
sequence may be a, t, g, c other or unknown

<400> SEQUENCE: 19

```
aagctttctt cgtcatataa tgagtaagat actttaacaa atgcgtattt tggtgttggt     60

ctgctaaagt aaatattatg tgctaaacca cctaaatcat gggctgtacc aaaaattgag    120

ccgtaagctc taataccagc aggttttgta tcccagattg cttgagcaac attatcattt    180

tgaccaccga ctacgacaat cttaaaagat tttggtggaa gaccttctga gttcgtctct    240

tcagtatcan tttcaacacc tgaagcatct gagacacctt gaanccttttt aacagcagct    300

acaattgcat ccaaagtccc tanaccaagt aactggtaaa gngtcnaaat atcnctgncn    360

aagttctgng tcagtttcct cggttctaac aattgntaag tcanacctgn tatagatgct    420
```

-continued

```
gtcaagacca tcaacaagtt gtctcaatct caataagagt cccaagctaa agcaggaata    480

gcaacaacct cttcagccac tacatctgag ataagttgta atctttgt                 528


<210> SEQ ID NO 20
<211> LENGTH: 517
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 20

aagcttcgtt ccaactacct ctcaagactt ttacaagtcc agcttcagaa gcagcagaaa     60

accccgcaaa tcgggtaact ttgtctttan ttgttggttt agctcttgct cgataacctt    120

tctcggcaag tttcctgatg agggatgttg cgtaggattt accagcagcg cctgggtctt    180

gagggataaa aataccagtt cgcttaccgt cactttcagc agtcaaatta atttgtgttt    240

cgactccaga gggtctatct ctaaatctta ctacatcaat gatataataa gcaaccgtct    300

tttttaagat ttaccatctt aacaactgct ggccaatccg ggttaaggnt aaacccaaga    360

tgggaaaagt tgctggctaa agtcccatgc tctgacatcg aatacatctt ctgggagtga    420

atcaacaatt tcacaccatt gnctttgcca aataagtttg aaccttctgc acgaagcctt    480

ccaagttacc gaaacgaagt cttgcaacgt ttacagg                             517


<210> SEQ ID NO 21
<211> LENGTH: 353
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 21

tgttaaagtt gtgaatgcaa aatcaccacg gctacaaggt acggtattta gtttcatctc     60

aagtgactga aaaccttgag tcagttcaat ttgtaactgc tccattacat aattgtggta    120

atgctcttta ggaataccat aagatgatgc tttctcagca tgatagcgtn naaacttctt    180

agcatacggt acaantncct tatcaatctc tgctaaagtn aaaccaccna attgctgtgc    240

anttgctgaa antnctacgt cnccaataac ctgcaacgct gacagtacag atttaggttc    300

acagtactcc atgccggaca tttcaaancc nccntttant actttaccna tgt           353


<210> SEQ ID NO 22
<211> LENGTH: 416
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 22

ggtgctccgt atgatgcagg ttcaattgct tggggtaacg cacagctaac tggcgtagct     60

gcttctctac agccatctaa tcagagacct ctgacaagta ttcagaantc agctttanat    120

gcacgtcact gtaactttat tgaccttgat ggtggtgttc cagtggttcg taganggatt    180

acttctggtg gggaatggat tnatatcatc cgtggtgttg actggttaaa atcngacctg    240

aaaacttctc tgagagactt gctaattaac cagaaaggtg gtaaggatta cttangatga    300

tactggtatt acccgtattc ccaagtcatt gaaacctctc tgcccancag cagtcnacag    360
```

-continued

```
aaacttcctg tcatcttana cacttaatgt tcctaaatcc tctcaanttg ctttgg        416


<210> SEQ ID NO 23
<211> LENGTH: 517
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 23

aagcttacca atctttctaa tcttagccca tcttttaacg tgaccttcat caccatcaat     60

cgggttgtca tatgtctcca tccatctgaa tccaaaaggt aagtgtcctt tcttctcact    120

gtaaaatgga actacaaaag gtgctaagat aactgctaag attgctgcca atgtttctag    180

caaagctaag aaaatccatg aagcatactt caagtatctc atttaaatag cctctttaaa    240

ttggcgcagg ataagggatt cgaacccccta ttaacagctt cgtagactgt tgctctatcc    300

atttgaacta atcctgctta cctacaagaa caccatacag tttttcacaa gagttgtttt    360

tacgcctgtt tttgaatgac gctataaact tttttgcaat tgatttatta ctcatagtgt    420

tctcctaaaa ttggtgttcc aagacggntt cgaaccgtca ctagtacaag ggttgagctt    480

gcatcctctg ccaattggga tactgggaca tggnact                             517


<210> SEQ ID NO 24
<211> LENGTH: 528
<212> TYPE: DNA
<213> ORGANISM: Bacteriophage
<220> FEATURE:
<223> OTHER INFORMATION: "n" at various positions throughout the
      sequence may be a, t, g, c other or unknown

<400> SEQUENCE: 24

aagctttgac ccagaaagac tgaataagtg ggcatcatgg gcagataagc gtggaattat     60

ctggtcagaa gtcactatgg aagccatgaa acgtgtctat gagggttgca ctacaaaaga    120

gatgcaccaa gccatgattg atgtttgtgt tgataagcaa actcaagagt actcagatat    180

ggctggacgg ctacttctgg gaattatcta caaagaagcc tttggaggtt tactaaggtt    240

cctacgctgg ttaccttcgn taaaaatatg gagagagcaa gactttggga gaagatggac    300

tattcacaag aaagagcttg aatatctgca agggtacatt gtgcactcan aaagatatct    360

cttacggtta tgcagtcttg aaacagttca agagacaagt atggtatccg tgatattaaa    420

acgggaagac tttttgagtc accacaattt atgtttatgg gtatggctat gaaagccttt    480

gagaagcaac caaagcaccg tagactgcaa gatgttatca agctgtac                 528
```